US011484271B2

(12) United States Patent
Engman et al.

(10) Patent No.: US 11,484,271 B2
(45) Date of Patent: Nov. 1, 2022

(54) ALERT PRESENTATION BASED ON ANCILLARY DEVICE CONDITIONS

(71) Applicant: West Affum Holdings Corp., Grand Cayman (KY)

(72) Inventors: Zoie R. Engman, Kirkland, WA (US); Joseph L. Sullivan, Kirkland, WA (US); David P. Finch, Bothell, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 140 days.

(21) Appl. No.: 16/997,804

(22) Filed: Aug. 19, 2020

(65) Prior Publication Data

US 2021/0052227 A1 Feb. 25, 2021

Related U.S. Application Data

(60) Provisional application No. 62/889,293, filed on Aug. 20, 2019.

(51) Int. Cl.
*G08B 21/00* (2006.01)
*A61B 5/00* (2006.01)
(Continued)

(52) U.S. Cl.
CPC .......... *A61B 5/7217* (2013.01); *A61B 5/2415* (2021.01); *A61B 5/25* (2021.01); *A61B 5/316* (2021.01); *A61B 5/6828* (2013.01); *A61B 5/746* (2013.01); *G01R 27/26* (2013.01); *G01R 29/26* (2013.01); *G08B 21/182* (2013.01); *A61N 1/3904* (2017.08)

(58) Field of Classification Search
CPC ..... A61B 5/7217; A61B 5/2415; A61B 5/316; A61B 5/25; A61B 5/6828; A61B 5/746; G01R 27/26; G01R 29/26; G08B 21/182; A61N 1/3904
USPC ........................................................ 340/660
See application file for complete search history.

(56) References Cited

U.S. PATENT DOCUMENTS

| 3,724,355 A | 4/1973 | Unger |
| 4,583,524 A | 4/1986 | Hutchins |

(Continued)

FOREIGN PATENT DOCUMENTS

WO  1998039061 A2  9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Zhen Y Wu

(57) ABSTRACT

In one embodiment, a method to differentiate between causes of noise in an electrocardiogram (ECG) signal. The method connecting to at least one sensing electrode and obtaining the ECG signal from the at least one sensing electrode. The method also includes detecting noise on the ECG signal and detecting ancillary conditions. The method also includes associating the noise on the ECG signal with at least one of the ancillary conditions and providing an actionable indication to a patient associated with the noise on the ECG signal.

20 Claims, 6 Drawing Sheets

(51) Int. Cl.

| | | |
|---|---|---|
| G08B 21/18 | (2006.01) | |
| G01R 29/26 | (2006.01) | |
| G01R 27/26 | (2006.01) | |
| A61B 5/25 | (2021.01) | |
| A61B 5/316 | (2021.01) | |
| A61B 5/24 | (2021.01) | |
| A61N 1/39 | (2006.01) | |

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bomn et al. |
| 5,353,793 | A | 10/1994 | Bomn |
| RE34,800 | E | 11/1994 | Hutchins |
| 5,394,892 | A | 3/1995 | Kenny |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,427,083 | B1 | 7/2002 | Owen et al. |
| 6,437,083 | B1 | 7/2002 | Owen et al. |
| 6,529,875 | B1 | 3/2003 | Nakajima |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 9,706,956 | B2 * | 7/2017 | Brockway ............ A61B 5/0006 |
| 10,271,739 | B2 * | 4/2019 | Freeman .............. A61B 5/4848 |
| 11,357,452 | B2 * | 6/2022 | Chakravarthy ....... A61B 5/7264 |
| 2003/0004547 | A1 * | 1/2003 | Owen .................. A61N 1/046 |
| | | | 607/5 |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0106191 | A1 * | 5/2011 | Bennett ................ A61N 1/37 |
| | | | 607/27 |
| 2011/0288604 | A1 | 11/2011 | Kaib et al. |
| 2011/0288605 | A1 * | 11/2011 | Kaib .................... A61B 5/021 |
| | | | 607/5 |
| 2012/0004563 | A1 * | 1/2012 | Kim ..................... A61B 5/259 |
| | | | 600/509 |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0005496 | A1 * | 1/2014 | Sison ................... A61B 5/721 |
| | | | 600/301 |
| 2014/0025131 | A1 | 1/2014 | Sullivan et al. |
| 2014/0070957 | A1 | 3/2014 | Longinotti-Buitoni et al. |
| 2014/0121565 | A1 * | 5/2014 | Kim ..................... A61B 5/7214 |
| | | | 600/595 |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0011901 | A1 * | 1/2015 | Warner ................ A61B 5/7203 |
| | | | 600/509 |
| 2015/0039053 | A1 | 2/2015 | Kaib et al. |
| 2015/0328472 | A1 | 11/2015 | Sullivan et al. |
| 2016/0004831 | A1 | 1/2016 | Carlson et al. |
| 2016/0082277 | A1 | 3/2016 | Foshee, Jr. et al. |
| 2016/0275936 | A1 * | 9/2016 | Thorn .................. G10L 13/08 |
| 2017/0071500 | A1 * | 3/2017 | Von Maydell ....... A61B 5/7246 |
| 2018/0117299 | A1 * | 5/2018 | Gustavson ........... A61B 5/0205 |
| 2018/0184933 | A1 * | 7/2018 | Sullivan .............. A61N 1/3904 |
| 2018/0185662 | A1 * | 7/2018 | Foshee, Jr. .......... A61N 1/3993 |
| 2020/0029911 | A1 * | 1/2020 | Chakravarthy ....... A61B 5/6802 |
| 2021/0038107 | A1 * | 2/2021 | Kim ..................... A61B 5/316 |

OTHER PUBLICATIONS

LIFECOR LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

\* cited by examiner

ALERT PRESENTATION BASED ON ANCILLARY DEVICE CONDITIONS

CROSS REFERENCE TO RELATED PATENT APPLICATIONS

This patent application claims benefit of U.S. Provisional Patent Application No. 62/889,293 filed Aug. 20, 2019 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to differentiate between causes of noise in an electrocardiogram (ECG) signal. The method connecting to at least one sensing electrode and obtaining the ECG signal from the at least one sensing electrode. The method also includes detecting noise on the ECG signal and detecting ancillary conditions. The method also includes associating the noise on the ECG signal with at least one of the ancillary conditions and providing an actionable indication to a patient associated with the cause of the noise on the ECG signal.

In some embodiments, the ancillary conditions may include one or more of an electrode impedance, an electrode leads-off indication, time since activation of one or more electrodes, patient input, patient location, patient motion, device motion, and environmental interference. In some embodiments the ancillary condition may include a right leg drive (RLD) leads-off indication.

In some instances, the method may include analyzing a preceding predetermined time history of a contact status of the at least one sensing electrode and determining when changes in the contact status occurred in preceding predetermined time history. In some instances, the preceding predetermined time history may be between approximately one minute and approximately thirty minutes. In some embodiments, the at least one sensing electrode may include two or more sensing electrodes and wherein analyzing the preceding predetermined time history includes analyzing a contact status of a specific electrode.

In some embodiments, the method may measure a DC voltage of the at least one sensing electrode at an input to a preamplifier, determine when the measured DC voltage passes a predetermined DC voltage threshold, and issue an alert to the patient flagging the at least one sensing electrode as high-impedance.

In some embodiments, the method may measure an AC impedance of the at least one sensing electrode, determine when the measured AC impedance passes a predetermined AC impedance threshold, and issue an alert to the patient flagging the at least one sensing electrode as high-impedance.

In some embodiments, the method may include establishing a library of known interference signals that cause noise on an ECG signal, comparing the noisy ECG signal to the library of known interference signals, and determining when the noisy ECG and known interference signal match a predetermined amount. In some embodiments, the method may include monitoring ancillary device conditions when noise is detected on the ECG signal, determining when the ancillary conditions are present, and facilitating differentiating root cause of the noise based at least in part on the ancillary conditions.

In another embodiment, a wearable cardioverter defibrillator (WCD) is described. The WCD includes a support structure wearable by a person and a processor coupled to the support structure. A discharge circuit is configured to discharge a stored electrical charge through a body of the patient. The discharge circuit in communication with the processor. The WCD also includes at least one sensing electrode in communication with the processor. The processor is configured to connect to the at least one sensing electrode, obtain an electrocardiogram (ECG) signal from the at least one sensing electrode, and detect noise on the ECG signal. The processor is also configured to detect ancillary conditions, associate the noise with at least one of the ancillary conditions, and provide an actionable indication to a patient associated with the ECG signal.

In some embodiments, the ancillary conditions may include one or more of an electrode impedance, electrode leads-off, patient motion, and environmental interference. In further embodiments, the ancillary condition may include a right leg drive (RLD) leads-off indication. In some embodiments, the processor may be further configured to analyze a preceding predetermined time history of a contact status of the at least one sensing electrode and determine when changes in the contact status occurred in preceding predetermined time history. In some embodiments, the preceding predetermined time history may be between approximately five minutes and approximately thirty minutes. In further embodiments, the preceding predetermined time history may be approximately ten minutes.

In some embodiments, the at least one sensing electrode may include two or more sensing electrodes. The processor may be further configured to analyze the preceding predetermined time history including analyzing a contact status of a specific electrode.

In some embodiments, the processor may be further configured to measure a DC voltage of the at least one sensing electrode at an input to a preamplifier, determine when the measured DC voltage passes a predetermined DC voltage threshold, and issue an alert to the patient flagging the at least one sensing electrode as high-impedance.

In some embodiments, the processor may be further configured to measure an AC impedance of the at least one sensing electrode, determine when the measured AC impedance passes a predetermined AC impedance threshold, and issue an alert to the patient flagging the at least one sensing electrode as high-impedance.

In some embodiments, the processor may be further configured to establish a library of known interference signals that cause noise on an ECG signal, compare the noisy ECG signal to the library of known interference signals, and determine when the noisy ECG and known interference signal match a predetermined amount. In some embodiments, the processor may be further configured to monitor ancillary device conditions when noise is detected on the ECG signal, determine when the ancillary conditions are present, and facilitate differentiating root cause of the noise based at least in part on the ancillary conditions.

In on embodiment, a method to differentiate between causes of noise in electrocardiogram (ECG) signals is described. The method includes positioning at least four ECG sensing electrodes to measure electrical activity of a heart of a person and receiving at least one ECG signal from at least three of the at least four ECG electrodes. The method includes detecting noise on the at least one ECG signal and detecting ancillary conditions. The method also includes associating the noise with at least one of the ancillary conditions and providing an actionable indication to a patient associated with the ECG signal.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
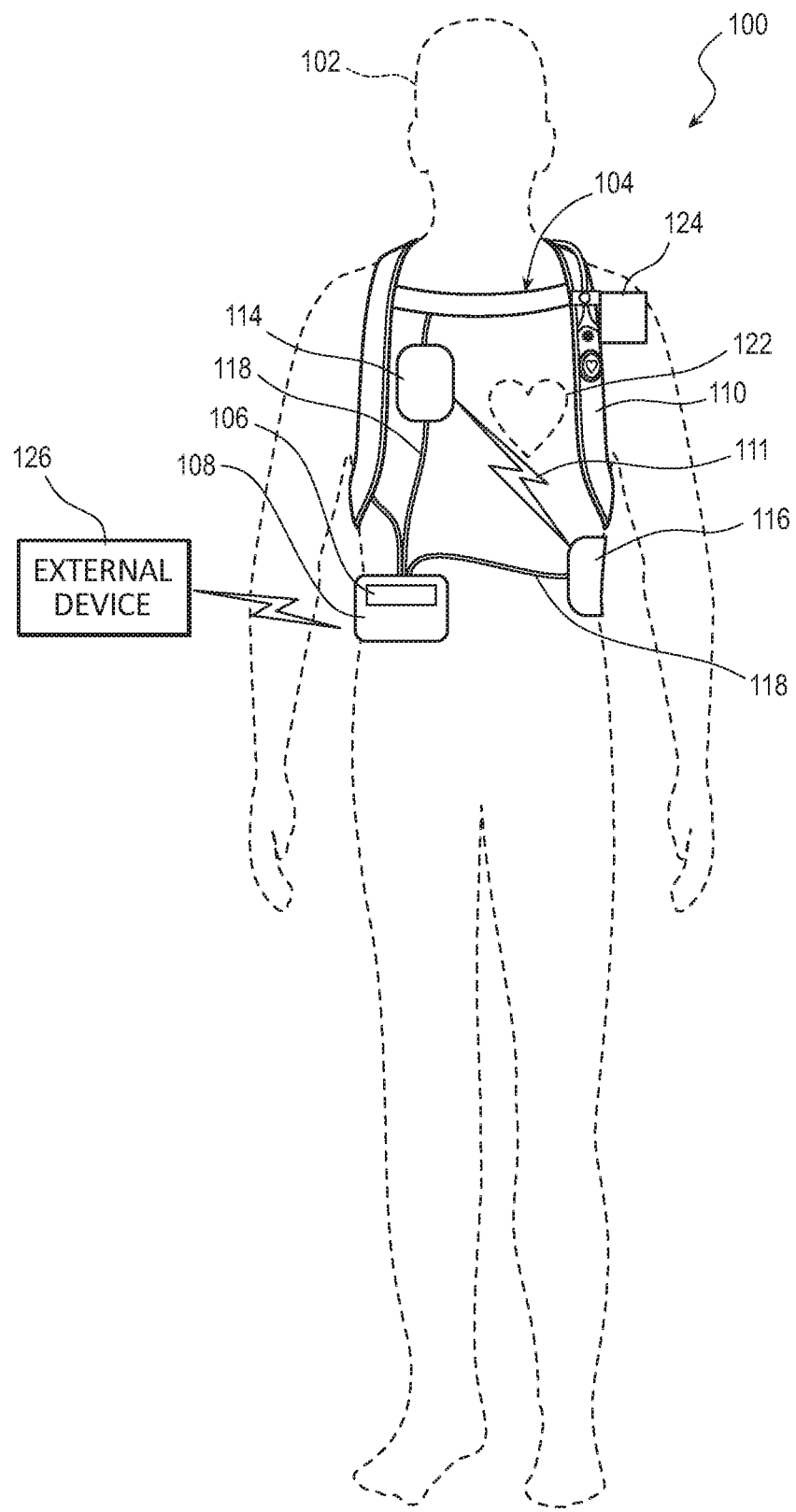
FIG. 1 is a diagram of a sample WCD system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest. When a patient wears a WCD, the WCD may need to alert the patient throughout its use, and in some instances, may need to shock the patient. However, in some instances, the WCD may detect a noisy condition and be unable to conduct an accurate rhythm analysis. The noisy condition may, in some instances, generate an alert to the patient. However, the patient may receive a noise alert without any clarifying information to correct the situation. These alerts may become a nuisance to the patient, who may ignore them. If the situation is ignored and the noisy condition continues, the patient's heart rate may not be monitored which, in some situations, may result in a shockable rhythm going undetected.

As discussed herein, noisy condition alerts with specific troubleshooting guidance may elicit better responses from the patient. The patient may view the alert and timely correct the condition to allow the WCD to resume heart rate analysis. For example, the WCD system may determine various issues or causes for the noisy signal and may direct the patient to correct the specific issue. The patient, when presented with an excessive noise alert, does not know what specifically caused the condition or how to quickly resolve it, resulting in the patient frustration with the lack of information and potential over-alerting of the patient.

A few potential causes of a noisy signal include leads-off causing lack of sufficient ECG electrode contact with the patient, drying out of the patient's skin causing lack of sufficient ECG electrode contact with the patient, motion causing excessive noise on the acquired signals from the ECG electrodes, environmental interference, such as EMI, causing excessive noise on the acquired signals from ECG electrodes, and the like. Each of these issues is detected as noise on the ECG signals and may be resolved by the patient in distinctly different ways. The ability of such embodiments to determine the root cause of the excessive noise is used to provide the patient with sufficient information to address or correct the issue in a timely manner. In contrast, embodiments of the present disclosure can differentiate between the causes of excessive noise condition and use that differentiation to provide the patient wearer with direction specific to the root cause of the noise. The specificity of the alert allows the patient to quickly correct the root cause of the issue, thus significantly reducing overall alarm burden.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the defibrillator 108 may connect with one or more external devices 126. For example, as shown in FIG. 1, the defibrillator 108 may connect to various external devices 126 such as a the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
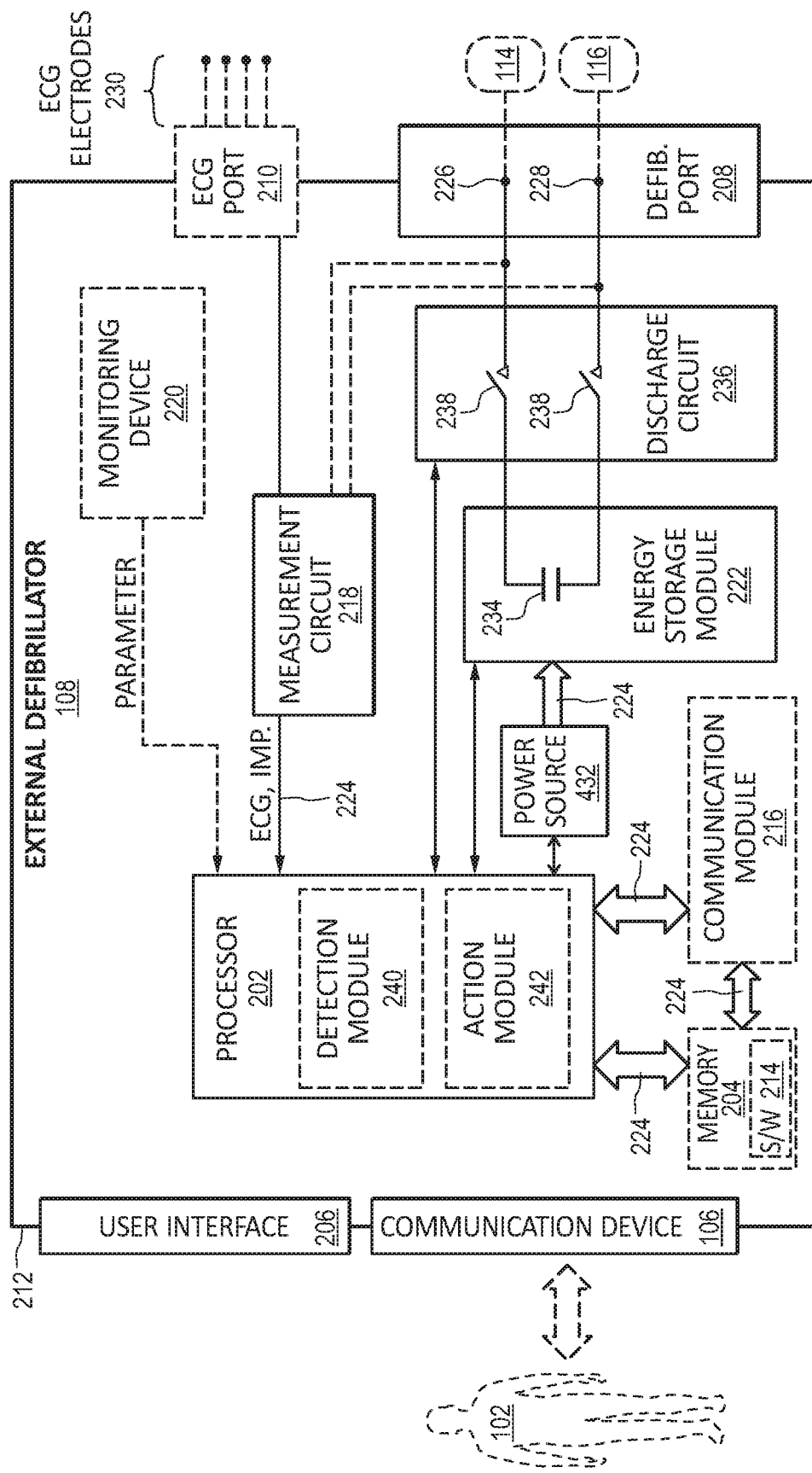
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine noisy signals, analyze noisy signals, alert patient, etc.). In some embodiments, the processor 202 may include an intelligent hardware device, e.g., a central processing unit (CPU), a microcontroller, an application-specific integrated circuit (ASIC), etc.

In embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g. a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g. defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g. leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g. WCD 104, FIG. 1), defibrillator 108, environmental parameters, or the like.

In some embodiments, the WCD system 104 may include an internal monitoring device 220 and an external monitoring device (e.g. external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of batter power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
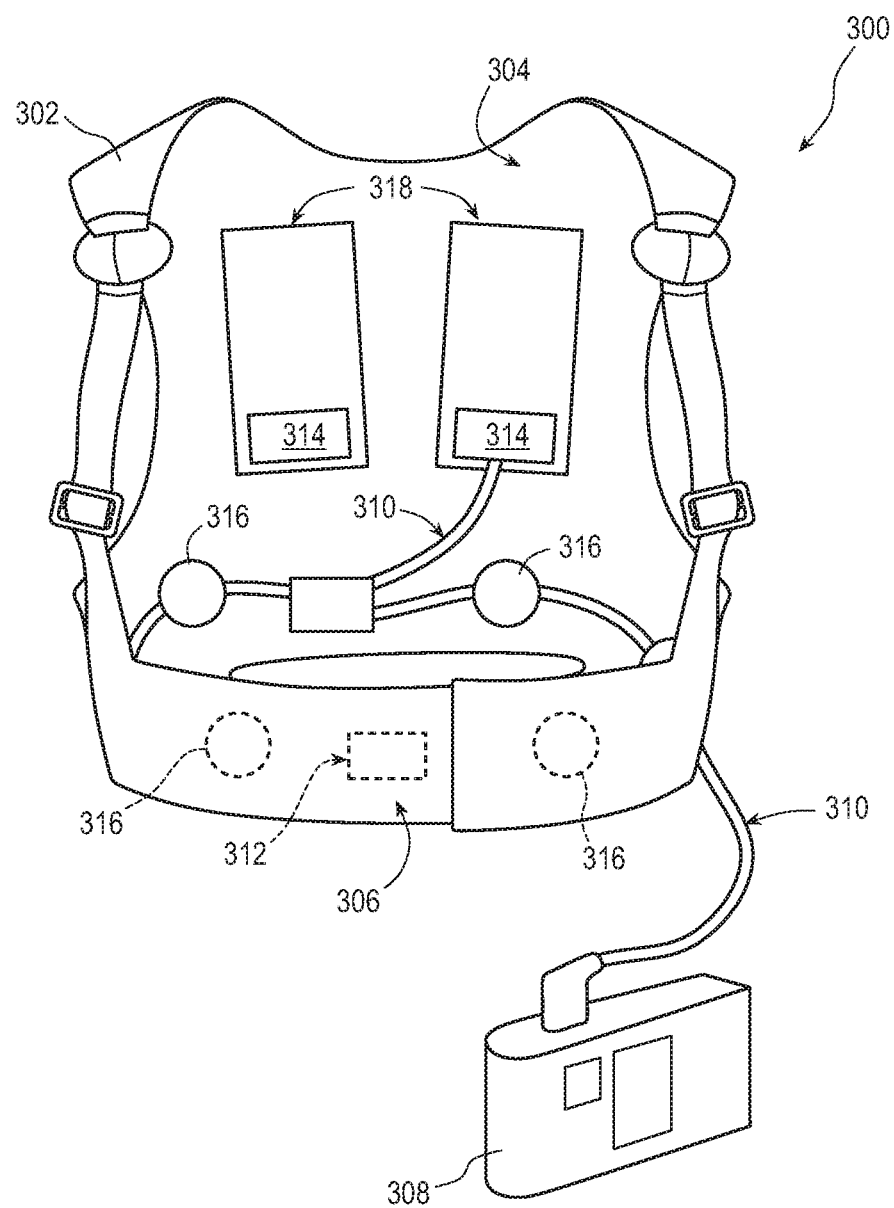
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of the chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor. The multiple ECG sensing electrodes 316 provide different vectors for sensing the ECG signal of the patient.

Figure 4:
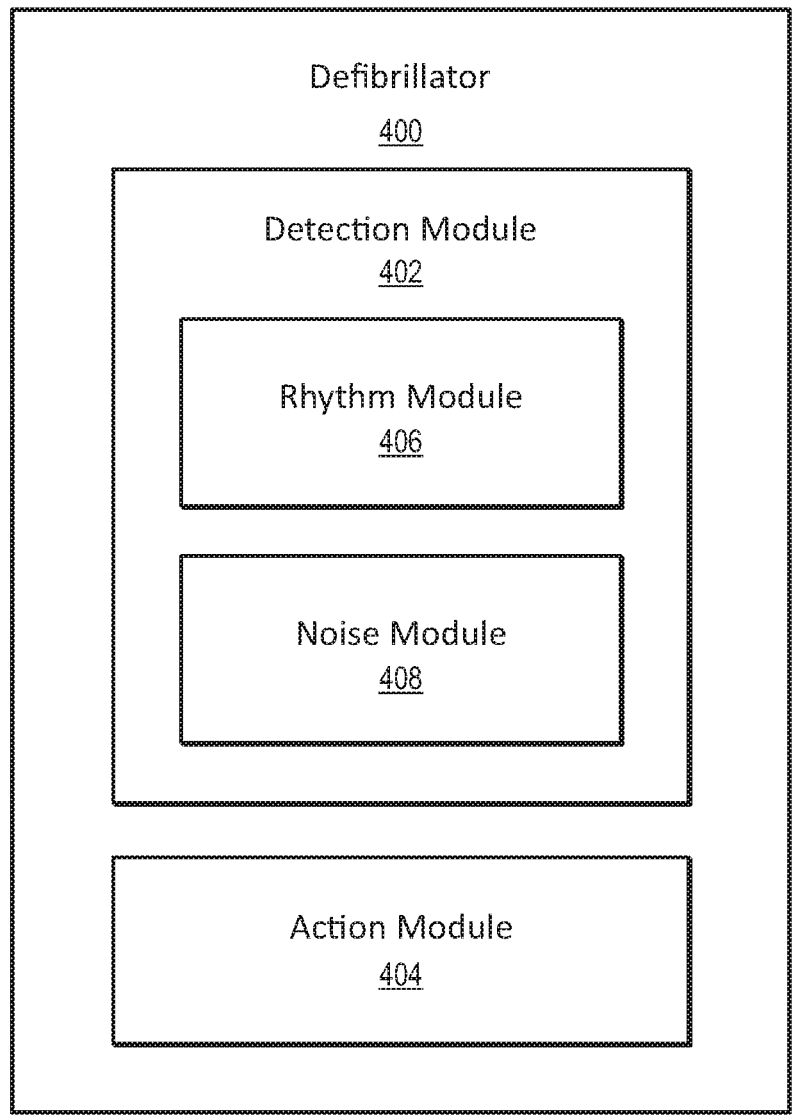
FIG. 4 is a is a block diagram of an example defibrillator in accordance with exemplary embodiments described herein.

FIG. 4 is a block diagram illustrating components of one example of a defibrillator 400. The defibrillator 400 may be an example of the defibrillator 108 described with reference to FIGS. 1 and 2 and/or a defibrillator 308 described with reference to FIG. 3. In this example, the defibrillator 400 has detection module 402 and an alert module 404. The detection module 402 may further include a rhythm module 406 and a noise module 408.

The detection module 402 may receive various data points to analyze for a health event. For example, the rhythm module 406 may receive various datapoints from the sensing electrodes to determine when a shockable rhythm is present. In some embodiments, the data may be too noisy to analyze. For example, various causes may be somehow affecting the incoming signal. If the rhythm module 406 cannot analyze the signal, the rhythm module 406 may relay the information to the noise module 408 which may perform a troubleshooting analysis to determine the potential root cause or causes of the noise on the ECG signal.

For example, the noise module 408 may analyze various data points in the system to determine a potential cause of the noise. The inability to analyze the signal may be from a number of causes including leads-off causing lack of sufficient ECG electrode contact with the patient, drying out of the patient's skin causing lack of sufficient ECG electrode contact with the patient, motion causing excessive noise on the acquired signal from the ECG electrodes, environmental interference causing excessive noise on the acquired signals from the ECG electrodes, an electrode impedance, time since activation of one or more electrodes, patient input, patient location, patient motion, device motion, and the like.

According to some embodiments, the noise module 408 may analyze a recent history of the ECG electrode contact status to determine the likelihood that drying of the ECG-skin interface is causing the algorithm's inability to analyze. For example, in some instances, upon entry to a noisy state, the noise module 408 analyzes a history of ECG electrode contact statuses. The analysis may review and determine a number of ECG electrode contact changes in a preceding predetermined duration of time. For example, the noise module 408 may analyze the electrode contact changes for approximately one to thirty minutes. In some embodiments, the noise module 408 may analyze the preceding ten minutes for electrode contact changes. The noise module 408 may determine one of a number of times electrodes lost contact with the patient's skin, a duration of time the electrode lost contact with the patient's skin, or both. The contact thresholds may depend upon the duration of time analyzed and the contact status analyzed. For example, the lost-contact threshold may be a percentage time duration of the total time duration of contact history reviewed. The lost-contact threshold may be 20% of the time. The lost-contact threshold could also be larger or smaller depending on various factors. In other embodiments, the lost-contact threshold may be a number of times the electrode lost skin contact. This threshold may be between approximately 2-5 times. In still further embodiments, the lost-contact threshold may be some combination thereof. For example, the noise module 408 may analyze both the number of times an electrode lost contact and the duration of that time. If any combination of thresholds is surpassed, the noise module 408 may initiate an alert to the patient. The noise module 408 may perform this analysis on one electrode, a specific electrode, all electrodes, or some combination thereof.

In some embodiments, the noise module 408 may analyze specific electrode contact changes in a preceding predetermined period of time. The predetermined period of time may be between approximately five and approximately thirty minutes, and in some embodiments, may be approximately ten minutes. In some embodiments, the noise module 408 may determine a dry-out condition is present when a predetermined threshold for lack of electrode contact is met. For example, the noise module 406 may determine a dry-out condition if an electrode lacks contact for five or more minutes of the preceding ten minutes after a noisy condition is present. In some embodiments, the noise module 408 may analyze the contact condition of the right leg drive (RLD) electrode to determine the patient's skin is too dry to make sufficient ECG electrode contact and readings. For example, the noise module 408 may determine the WCD did not register any readings from the RLD electrode for five or more of the preceding ten minutes after a noisy condition is detected. This threshold may mean the contact point has dried out and requires patient attention. In some embodiments, the ECG preamplifiers in the RLD electrode provides the return path for the leads-off current for all of the other ECG electrodes. If multiple electrodes are at a relatively high impedance and are approaching their leads-off threshold then the RLD electrode may saturate and indicate RLD off before the other leads give a leads-off indication. As such, RLD off can provide an early indication that ECG electrode impedance is getting relatively high. If noise is detected on the ECG signal when RLD is off, then in some embodiments, the WCD may prompt the patient to take steps to reduce the electrode impendence. In a WCD system that uses dry contact electrodes, then appropriate remedy may be to add moisture to that electrode.

In some embodiments, the noise module 408 may analyze the time since activation of one or more electrode. For example, due to the nature of dry electrodes, it can take time for the skin-electrode interface to develop sufficient moisture for a noise-free ECG signal. The noise module 408 may monitor a time since the defibrillator was activated to determine if a noisy ECG signal is a result of poor skin-electrode contact. For example, depending on the patient and environmental factors such as humidity, the skin-electrode contact may quickly develop sufficient moisture for a noise-free ECG signal. In other embodiments, it may take a few minutes for the moisture to build and create sufficient skin to electrode contact. The noise module 408 may monitor these conditions as well as patient history to determine if a noise alert should be issued to the patient. In some embodiments, if a predetermined period of time has passed, the noise module 408 may provide an indication to the patient to add moisture to the skin for sufficient skin-electrode contact.

In another embodiment, the noise module 408 may analyze the impedance of an ECG electrode. For example, in some embodiments, a WCD system may use a DC leads-off current. The DC voltage may be measured at the input to the preamplifier which may provide an indication of the electrode impedance. The preamplifier may be located between the ECG sensing electrode and the defibrillator and may aid in signal preservation. If the DC voltage surpasses a predetermined threshold, then the electrode may be flagged as being high impedance. The threshold may change from patient to patient. In some embodiments, the threshold may be approximately 100 nA. In a leads-off condition, the threshold may be approximately 10 Mohm. This could be measured with a 1 volt drop through the electrode. In other embodiments, the threshold may range from approximately 10 nA up to 10 μA. The DC voltage threshold may be exceeding an absolute level or approaching a dynamic limit of the preamplifier. In other embodiments, the WCD system may use an AC leads-off current. The noise module 408 may establish a threshold for the AC impedance before an electrode is considered high impedance. The threshold may be range from approximately 100 k ohms up to 100 Mohms. A lower threshold may ensure that an electrode that measures "on" would truly give a good signal, but an electrode that measures "off" might actually be touching the skin and usable. In other embodiments, a higher may ensure that an electrode measuring "off" is truly off, but if it measures "on" may cause noise on the ECG signal. In both DC and AC leads-off embodiments, the noise module 408 may determine an electrode to be high-impedance prior to reaching the leads-off threshold. If ECG noise is detected while one or more electrodes is flagged as high impedance, then in some embodiments, the noise module 408 may prompt the patient to take steps to reduce the impedance. This may include reaffixing the electrode to the patient's skin to ensure proper contact and ECG readings.

In some embodiments, ECG preamplifiers in the RLD electrode provide the return path for leads-off current for all of the other ECG electrodes. If multiple electrodes are at a relatively high impedance and are approaching their leads-off threshold then the RLD electrode may saturate and indicate the RLD is off. For example, moderate increases in the RLD electrode resistance may cause the RLD electrode to saturate which may cause ECG noise because the RLD amplifier will no longer be capable of attenuating noise on the body. Therefore, in some embodiments, the noise module 408 may analyze the RLD electrode in addition to or instead of analyzing other electrodes.

In some embodiments, the noise module 408 may also analyze patient motion to assess a noisy signal. For example, the WCD includes an accelerometer. The noise module 408 may analyze a history of accelerometer data to for a preceding period of time. The preceding period of time may be between approximately one minute and ten minutes, and in some embodiments, may be approximately two minutes. The noise module 408 may determine, based on accelerometer readings, that there is a high likelihood that the patient is moving which may be the cause of the algorithm's inability to analyze the ECG signal. In some embodiments, the noise module 408 may assess the type of motion as discussed in U.S. patent application Ser. No. 16/158,174 filed on Oct. 11, 2018 and incorporated herein in its entirety. The assessment of the type of motion could decide to alert the user if the motion cannot be classified but not alert the user if the motion is due to a classifiable activity that indicates that the patient's physiologic health is not of concern.

In some embodiments, if the WCD system has more than one accelerometer, the noise module 408 may compare accelerometer readings to determine which noise indication is present. For example, in some embodiments, a first accelerometer is located on the patient's torso and a second accelerometer is located within the primary electronics module of the device. The noise module 408 could compare the accelerometer signals to determine the cause of the noise. For example, if the patient is exercising, the accelerometers may have similar or vastly different signals. For example, the patient may be jogging on a treadmill and the electronics module may be placed on a surface. In another example, the patient may be playing basketball and the accelerometer signals may substantially match.

In still further embodiments, the noise module 408 may determine the presence of environmental interference by analyzing the history of signals over a predetermined preceding period of time and comparing the signal history to a library of known interference. The library of known interference may be established based on known WCD recordings from a collective pool of patients or may be specific to the particular patient. The noise module 408 may compare the signal patterns to a known pattern caused by a specific type of interference. If the noise module 408 finds a match, the noise module 408 may initiate an alert to the patient. When comparing profiles, the noise module 408 will determine a match if the patterns have approximately 70% or higher correlation. For example, the presence of electromagnetic interference (EMI) from medical equipment may be detected and the patient may be instructed to move away from the source of interference. In another example, the patient may be exercising, and the movement may be interrupting the ECG signal. The patient may be instructed to pause exercising or movement for the WCD to obtain a clear signal.

In some embodiments, the noise module 408 may determine environmental interference based on patient location. For example, the noise module 408 may determine a location of the patient and use that information to determine the location's influence on the type of noise present on the ECG signal. For example, if the patient is located in an area known to emit EMI, the noise module 408 may determine the noise is associated with EMI and indicate such to the patient. In another example, if the patient is located at a fitness center, the device may present a noise indication associated with patient motion.

Once the noise module 408 has determined one or more potential causes of noise on the ECG signal, the noise module 408 may issue an alarm. The alarm may provide an actionable indication to the patient. The actionable indication may indicate to the patient what is causing noise in the system and to address it. In some embodiments, the alert may provide step by step instructions to address the root cause. The step by step instructions may walk the patient through the troubleshooting process. Once the troubleshooting process is complete, the rhythm module 406 may rerun its analysis to determine if noise is still present on the ECG signals. If noise is still present, the noise module 408 may rerun the troubleshooting analysis to determine if the same root cause is present or if a new cause has presented itself. The defibrillator 400 may continue to cycle through this process until the noise is eliminated.

In further embodiments, the noise module 408 may use patient input to adjust the noise alert. For example, the noise module 408 may present noise alerts in a predetermined sequential order. The patient may respond to the alerts to acknowledge or indicate that they performed the action requested by the noise module 408. Once the patient response is acknowledged, the rhythm module 406 may rerun its analysis to determine if noise is still present on the ECG signals. If the noisy condition is still present, the noise module 408 may present a second alert to the patient requiring a different action to assess the noise on the ECG signal. The noise module 408 and rhythm module 406 may cycle through these steps to resolve the noisy signal.

Figure 5:
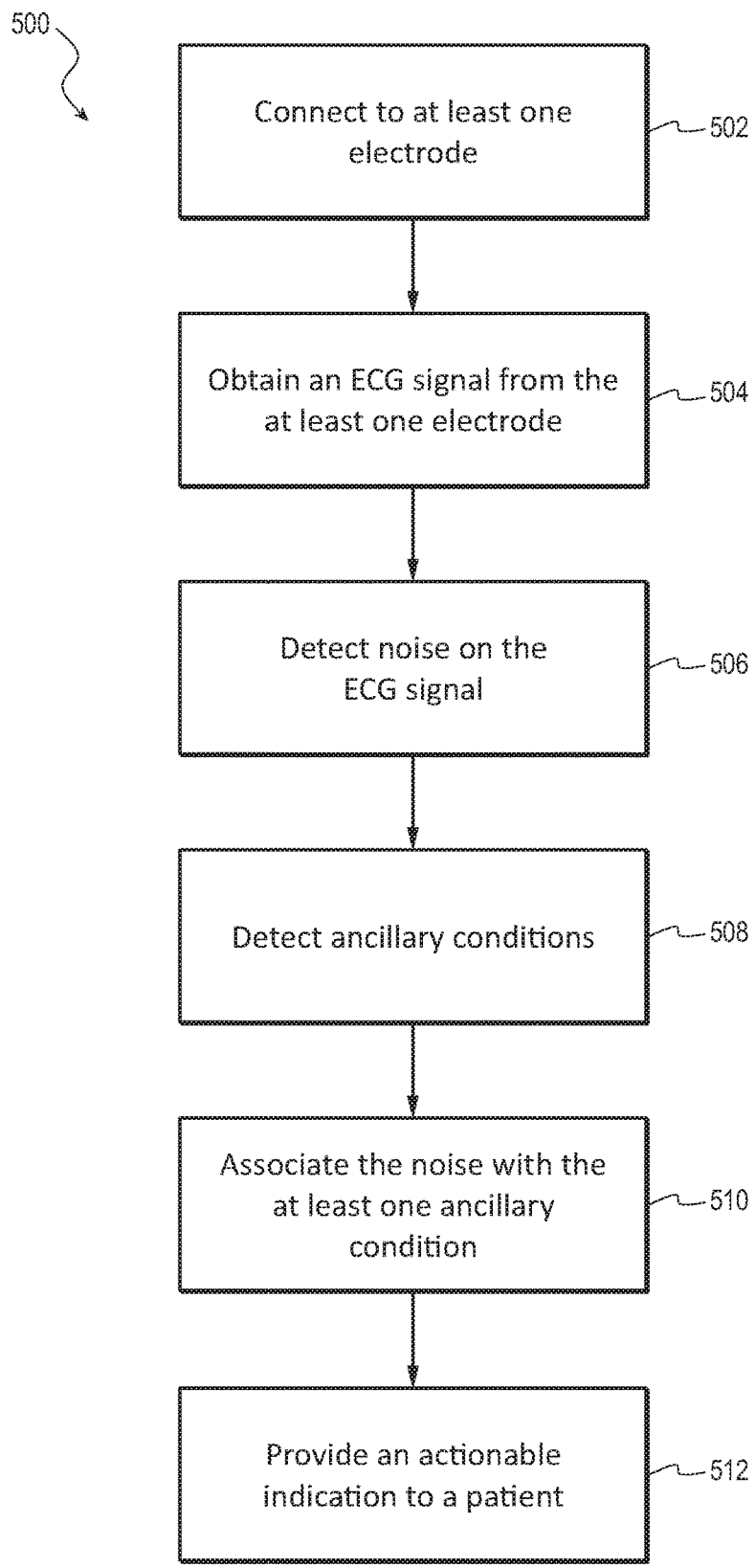
FIG. 5 is an exemplary flow diagram in accordance with exemplary embodiments described herein.

FIG. 5 is a flow chart illustrating an example of a method 500 for WCD systems, in accordance with various aspects of the present disclosure. For clarity, the method 500 is described below with reference to aspects of one or more of the systems described herein.

At block 502, the method 500 may connect to at least one sensing electrode. The sensing electrode may be a part of a WCD system. In some instances, the sensing electrode may be coupled to a patient's skin. At block 504, the method 500 may obtain an ECG signal from the at least one sensing electrode. The method 500 may analyze the ECG signal for a shockable heart rhythm. In some embodiments, if the ECG signal is unclear, or has some level of interference or noise, at block 506, the method 500 may detect noise on the ECG signal. The noise may prevent the method 500 from adequately analyzing the heartbeat for a shockable rhythm. Therefore, at block 508, the method 500 may detect ancillary conditions. The ancillary conditions may include one or more of an electrode impedance, an electrode leads-off, patient motion, environmental interference, and the like. IN some embodiments, the ancillary condition may additionally or alternatively include a RLD leads-off indication. At block 510, the method 500 may associate the noise with at least one ancillary condition. In some embodiments, more than one condition may be present. Once the method 500 has determined a likely root-cause of the noise, at block 512, the method 500 may provide an actionable indication to the patient. The actionable indication to the patient may be an alert. In some embodiments, the actionable indication may pinpoint the root cause of noise and provide steps for the patient to take to reduce and/or eliminate the noise on the ECG signal.

Thus, the method 500 may provide for a method of determining a root-cause of noise in an ECG signal. It should be noted that the method 500 is just one implementation and that the operations of the method 500 may be rearranged or otherwise modified such that other implementations are possible.

Figure 6:
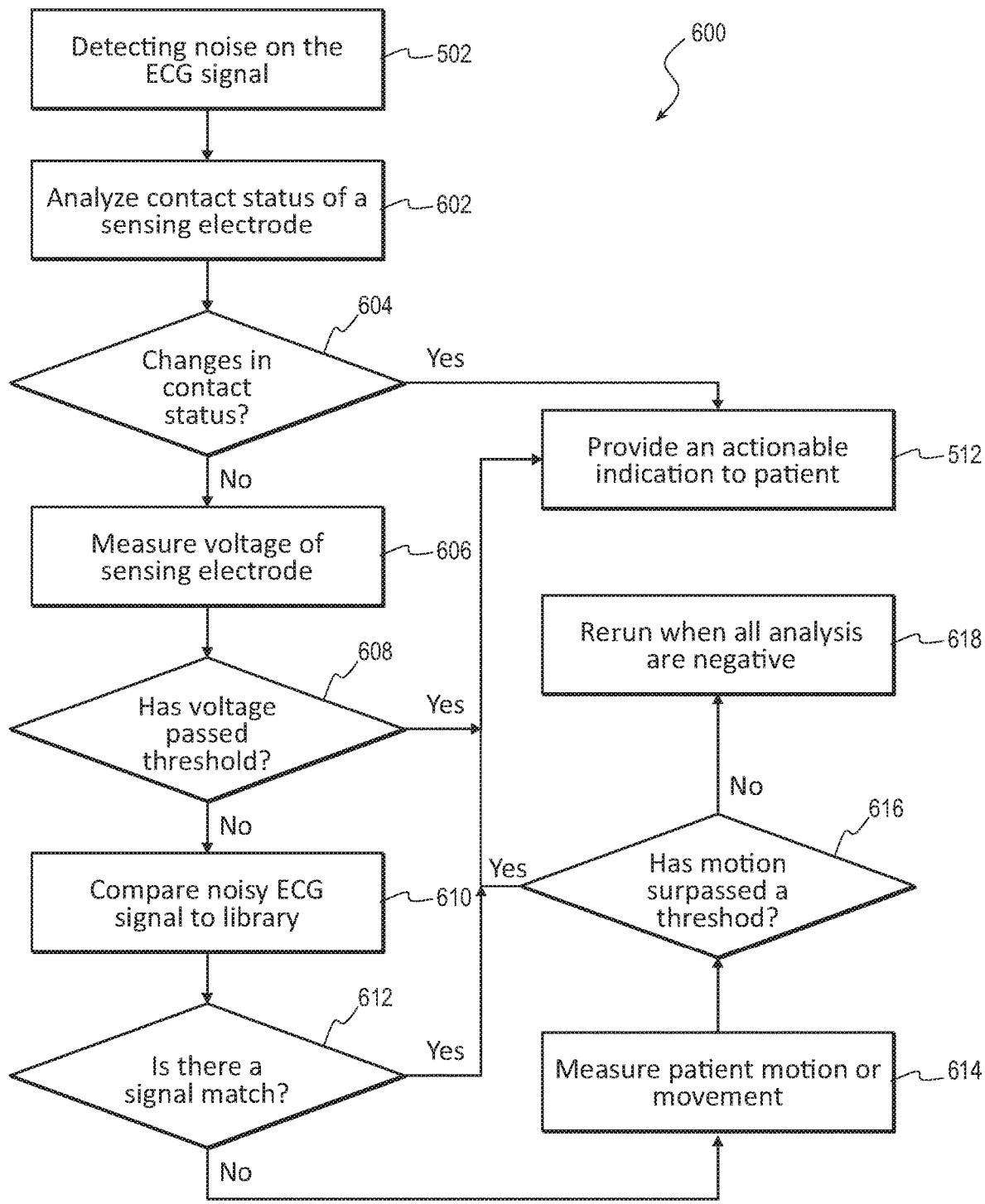
FIG. 6 is another exemplary flow diagram in accordance with exemplary embodiments described herein.

FIG. 6 is a flow chart illustrating an example of a method 600 for WCD systems, in accordance with various aspects of the present disclosure. For clarity, the method 600 is described below with reference to aspects of one or more of the systems described herein.

At block 502, the method 600 may detect a noise on an ECG signal. At block 602, the method 600 may analyze a contact status of a sensing electrode associated with the ECG signal. For example, the method 600 may review the connection history of the electrode for a time period prior to receiving the noisy ECG signal. The method 600 may review up to thirty minutes of historical contact status. In other embodiments, the method 600 may review more or less time to determine a history of contact status changes of the electrode. In some embodiments, the method 600 may analyze all of the electrode contact statuses, a particular electrode, or an electrode associated with the ECG signal. At block 604, the method 600 may determine if there have been any changes in a contact status. If the amount or duration of contact status changes exceeds a predetermined threshold, the method 600 may, at block 512, provide an actionable indication to the patient. The predetermined threshold may be an amount of times an electrode lost contact with the skin or may be a duration of lost contact. The threshold may also depend up the duration of time analyzed. For example, if five minutes preceding is analyzed, the threshold may be lower than if the thirty minutes preceding is analyzed. If fifteen minutes is analyzed, the thresholds may be set at three electrode contact losses and/or three minutes of electrode leads off or some combination thereof.

In some embodiments, the threshold may be patient dependent. For example, the threshold may be deviations from normal contact behavior on one minute of a clean ECG signal. In this instance, the method 600 would determine a value for the typical contact change events in a one minute of clean ECG signal for the specific patient. This typical contact value would become the threshold. This approach allows for the typical contact value to be updated to account for changes in the garment fit on the patient. For example, a patient may average zero contact changes events in one minute of clean ECG signal. If a noisy condition occurs (one-minute threshold) and a two-minute history shows any contact change events, the method 600 would consider the noise threshold satisfied. In another example, the patient may average ten contact change events in a one minute of clean ECG signal. If a noisy condition occurs (one-minute threshold) and a two-minute history shows significantly more contact status changes, perhaps fifteen contact changes or more, the threshold would be satisfied.

In some embodiments, if no changes in contact status are detected, at block 606, the method 600 may measure the voltage of one or more sensing electrodes. For example, the method 600 may measure a DC voltage of at least one sensing electrode at an input to a preamplifier. The method 600 may then determine if the DC voltage has surpassed a predetermined DC voltage threshold. The predetermined DC voltage threshold may include either exceeding an absolute level or approaching a dynamic limit of the preamplifier. In some embodiments, an absolute level may be approximately 1.1 V. In other embodiments, the dynamic limit of the preamplifier may be approximately 1.3V. In other embodiments, the method 600 may measure AC impedance to determine a leads off. For example, the method 600 may set an AC impedance threshold which may trigger an AC leads-off alarm. The AC impedance threshold may vary, but in some embodiments, ranges from 100 kOhms to 100 MOhms. At block 608, the method 600 may determine if the DC voltage, or AC impedance, has surpassed the corresponding threshold. If the corresponding threshold has been surpassed, then at block 512, the method 600 may provide an actionable indication to the patient. If the threshold has not been surpassed, then the method 600 may continue to block 610.

At block 610, the method 600 may compare the noisy ECG signal to a library of known interference signals. In some embodiments, the library of known interference signals may be a pre-populated library that may be generic. In other embodiments, the library may be specific to known causes relating to the specific patient. In still further embodiments, the library may be a combination of both pre-populated generic causes and causes or signals specific to the patient. The method 600 may compare the signals looking for a match. The match may not be a perfect or 100% match, but rather, may be a percentage match. For example, the ECG signals may align approximately 60-90%. In another example, the method 600 may not determine a percentage match but rather may determine a best match regardless of the accuracy of the match. In other embodiments, the method 600 may look not for alignment of ECG signals but for known tracers or signals of interference such as frequency, amplitude, slope, and such. For example, interference caused by EMI from medical equipment may have distinct markers on the ECG signal. At block 612, the method 600 may locate these markers, determine a signal match, and at block 512, provide an actionable indication to the patient. If, at block 612, the signals do not match, then the method 600 may move to block 614.

At block 614, the method 600 may measure patient motion or movement. For example, the WCD system may include an accelerometer. The method 600 may analyze accelerometer data to determine the likelihood that patient motion is the cause of the noise on the ECG signal. In some embodiments, the method 600 may analyze the accelerometer data in real-time. In other embodiments, the method 600 may analyze a set time history of accelerometer data. In still further embodiments, the method 600 may analyze some combination thereof. At block 616, if the accelerometer motion data exceeds a motion threshold, the method 600 may, at block 512, provide an actionable alert to the patient. If, at block 616, the motion threshold has not been exceeded, then the method 600 may proceed to block 618.

At block 618, if all of the analysis is negative but the system is still experiencing noise on the ECG signal, the method 600 may rerun. In some embodiments, the method 600 may rerun a predetermined number of times, for example approximately 2-5. If, after the method 600 has cycled through several times and the ECG signal is still experiencing noise, the method 600 may issue an alert to the patient. The alert may indicate to the patient to run a full diagnostic on the system.

Thus, the method 600 may provide for determining the root cause of noise in an ECG signal. It should be noted that the method 600 is just one implementation and that the operations of the method 600 may be rearranged or otherwise modified such that other implementations are possible. For example, the method 600 is shown in a sequential order. However, the sequence of the method 600 could be rearranged into any order. In other embodiments, each troubleshooting step [e.g., the troubleshooting described in blocks 602-604, blocks 606-608, blocks 610-612, and blocks 614-616] could be performed simultaneously or concurrently.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to differentiate between causes of noise in an electrocardiogram (ECG) signal, the method comprising:

receiving the ECG signal from at least one sensing electrode;
detecting noise on the ECG signal;
detecting ancillary conditions;
associating the noise on the ECG signal with at least one of the ancillary conditions; and
providing an actionable indication to a patient associated with the cause of the noise on the ECG signal, wherein detecting the ancillary conditions comprises:
  measuring a DC voltage of the at least one sensing electrode at an input to a preamplifier,
  determining when the measured DC voltage passes a predetermined DC voltage threshold, and
  issuing an alert to the patient flagging the at least one sensing electrode as high-impedance.

2. The method of claim 1, wherein the ancillary conditions include one or more of an electrode leads-off indication, patient input, patient location, patient motion, device motion, and environmental interference.

3. The method of claim 1, wherein the ancillary conditions include a right leg drive (RLD) leads-off indication.

4. The method of claim 1, further including:
analyzing a preceding time history of a contact status of the at least one sensing electrode; and
determining when changes in the contact status occurred in preceding time history.

5. The method of claim 4, wherein the preceding time history is between approximately one minute and approximately thirty minutes.

6. The method of claim 4, wherein the at least one sensing electrode includes two or more sensing electrodes and wherein analyzing the preceding time history includes analyzing a contact status of a specific electrode.

7. The method of claim 1, further comprising:
accessing a library of known interference signals that cause noise on an ECG signal;
comparing the noisy ECG signal to the library of known interference signals; and
determining when the noisy ECG and known interference signal meets a predetermined amount.

8. The method of claim 1, further comprising:
monitoring ancillary device conditions when noise is detected on the ECG signal;
determining when the ancillary conditions are present; and
facilitating differentiating root cause of the noise based at least in part on the ancillary conditions.

9. The method of claim 1, wherein the ancillary conditions include time since activation of the at least one sensing electrode.

10. A wearable cardioverter defibrillator (WCD) system, comprising:
an energy storage device;
a therapy electrode;
a processor;
a discharge circuit configured to discharge a stored electrical charge from the energy storage device via the therapy electrode through a body of a patient while the patient is wearing the WCD, the discharge circuit communicatively coupled with the processor; and
at least one sensing electrode in communication with the processor;
the processor configured to:
  receive an electrocardiogram (ECG) signal from at least one sensing electrode;
  detect noise on the ECG signal;
  detect ancillary conditions;
  associate the noise with at least one of the ancillary conditions;
  provide an actionable indication to a patient associated with the ECG signal, wherein detect ancillary conditions comprises the processor further configured to:
    measure a DC voltage of the at least one sensing electrode at an input to a preamplifier;
    determine when the measured DC voltage passes a predetermined DC voltage threshold; and
    issue an alert to the patient flagging the at least one sensing electrode as high-impedance.

11. The WCD system of claim 10, wherein the ancillary conditions include one or more of an electrode leads-off, patient motion, and environmental interference.

12. The WCD system of claim 10, wherein the ancillary conditions include a right leg drive (RLD) leads-off indication.

13. The WCD system of claim 12, wherein the processor is further configured to:
analyze a preceding time history of a contact status of the at least one sensing electrode; and
determine when changes in the contact status occurred in preceding time history.

14. The WCD system of claim 13, wherein the preceding time history is between approximately one minute and approximately thirty minutes.

15. The WCD system of claim 10, wherein the processor is further configured to:
access a library of known interference signals that cause noise on an ECG signal;
compare the noisy ECG signal to the library of known interference signals; and
determine when the noisy ECG and known interference signal meets a predetermined amount.

16. The WCD system of claim 10, wherein the processor is further configured to:
monitor ancillary device conditions when noise is detected on the ECG signal;
determine when the ancillary conditions are present; and
facilitate differentiating root cause of the noise based at least in part on the ancillary conditions.

17. A method to differentiate between causes of noise in an electrocardiogram (ECG) signal, the method comprising:
receiving the ECG signal from at least one sensing electrode;
detecting noise on the ECG signal;
detecting ancillary conditions;
associating the noise on the ECG signal with at least one of the ancillary conditions;
providing an actionable indication to a patient associated with the cause of the noise on the ECG signal, wherein detecting the ancillary conditions comprises:
  measuring an AC impedance of the at least one sensing electrode;
  determining when the measured AC impedance passes a predetermined AC impedance threshold; and
  issuing an alert to the patient flagging the at least one sensing electrode as high-impedance.

18. The method of claim 17, further comprising:
accessing a library of known interference signals that cause noise on an ECG signal;
comparing the noisy ECG signal to the library of known interference signals; and
determining when the noisy ECG and known interference signal meets a predetermined amount.

19. A wearable cardioverter defibrillator (WCD) system, comprising:
- an energy storage device;
- a therapy electrode;
- a processor; and
- a discharge circuit configured to discharge a stored electrical charge from the energy storage device via the therapy electrode through a body of a patient while the patient is wearing the WCD, the discharge circuit communicatively coupled with the processor;
- at least one sensing electrode communicatively coupled with the processor;
- the processor configured to:
  - receive an electrocardiogram (ECG) signal from at least one sensing electrode;
  - detect noise on the ECG signal;
  - detect ancillary conditions;
  - associate the noise with at least one of the ancillary conditions;
  - provide an actionable indication to a patient associated with the ECG signal, wherein detect ancillary conditions comprises the processor further configured to;
    - measure an AC impedance of the at least one sensing electrode;
    - determine when the measured AC impedance passes a predetermined AC impedance threshold; and
    - issue an alert to the patient flagging the at least one sensing electrode as high-impedance.

20. The WCD system of claim 19, wherein the processor is further configured to:
- access a library of known interference signals that cause noise on an ECG signal;
- compare the noisy ECG signal to the library of known interference signals; and
- determine when the noisy ECG and known interference signal meets a predetermined amount.

* * * * *